United States Patent
Ochiai et al.

(10) Patent No.: US 10,426,813 B2
(45) Date of Patent: Oct. 1, 2019

(54) METHOD TO ENHANCE ENDURANCE

(75) Inventors: Masayuki Ochiai, Tsukuba (JP); Koji Morishita, Tsukuba (JP); Miho Komatsu, Tsukuba (JP); Yoichiro Sugimura, Tokyo (JP); Kentaro Sugimura, legal representative, Chiyoda-ku (JP)

(73) Assignee: KYOWA HAKKO BIO CO., LTD., Chiyoda-Ku, Tokyo (JP)

(*) Notice: Subject to any disclaimer, the term of this patent is extended or adjusted under 35 U.S.C. 154(b) by 354 days.

(21) Appl. No.: 13/508,163

(22) PCT Filed: Nov. 5, 2010
(Under 37 CFR 1.47)

(86) PCT No.: PCT/US2010/055638
§ 371 (c)(1),
(2), (4) Date: Dec. 19, 2012

(87) PCT Pub. No.: WO2011/057082
PCT Pub. Date: May 12, 2011

(65) Prior Publication Data
US 2013/0225509 A1 Aug. 29, 2013

Related U.S. Application Data

(60) Provisional application No. 61/259,031, filed on Nov. 6, 2009.

(51) Int. Cl.
*A61K 38/05* (2006.01)
*A61K 31/198* (2006.01)

(52) U.S. Cl.
CPC ............ *A61K 38/05* (2013.01); *A61K 31/198* (2013.01)

(58) Field of Classification Search
CPC .............................. A61K 31/198; A61K 38/05
See application file for complete search history.

(56) References Cited

U.S. PATENT DOCUMENTS

2010/0168040 A1 7/2010 Komatsu et al.
2010/0234308 A1 9/2010 Komatsu et al.

FOREIGN PATENT DOCUMENTS

| EP | 0540462 A1 * | 10/1992 | ........... A61K 31/195 |
|---|---|---|---|
| WO | 2007108530 A1 | 9/2007 | |
| WO | 2007119503 A1 | 10/2007 | |

OTHER PUBLICATIONS

Espacenet Document stating WO2007108530 Description not availbale and corresponding description is from US2010168040 A1.*
UniProtKB/Swiss-Prot, Accession No. P01275, Glucagon sequence, p. 6, Feb. 6, 2007.*
Jes B Sørensen, Exercise on Prescription: trial protocol and evaluation of outcomes, BMC Health Services Research 2007, 7:36.*
William Mathieu Cheramie, Effects of Aerobic and Anaerobic Training Protocols on 4000M Track Cycling Time Trial, A Thesis, Louisiana State University, 2004.*
Advocare, www.wrestlingcampstore.com/images/Rehydrate_facts.pdf, AdvoCare International, L.P., pp. 1-3, published online Mar. 14, 2006.*
Contrata, www.howtodothings.com/sports-recreation/how-to-recognize-the-signs-and-symptoms-of-overtraining, published online Jun. 2008, pp. 1-4.*
Horleys, www.horleys.com/Resources/Resources/Resources%20-%20Dehydration%20%26%20Fluid%20Replacement, Dehydration and Fluid Replacement, published online Feb. 1, 2000.*
Cruzat et al., "Effects of oral supplementation with glutamine and alanyl-glutamine on glutamine, glutamate, and glutathione status in trained rats and subjected to long-duration exerise", Nutrition, Elsevier Inc., vol. 25, No. 4, pp. 428-435, Apr. 1, 2009.
Rogero et al., "Effect of alanyl-glutamine supplementation on plasma and tissue glutamine concentrations in rats submitted to exhaustive exercise", Nutrition, Elsevier Inc., vol. 22, No. 5, pp. 564-571, May 1, 2006.
Rogero et al., "Effect of L-glutammine and L-alanyl-L-glutamine supplementation on the response to delayed-type hypersensitivity test (DTH) in rats submitted to intense training", Revista Brasileira De Ciencias Farmaceuticas/Brazilian Journal of Pharmaceutical Sciences, vol. 38, No. 4, pp. 487-497, Oct. 2002.
Supplementary European Search Report dated Mar. 18, 2013 in European Patent Application No. EP10829155 corresponding to U.S. Appl. No. 13/508,163.
P.L. Greenhaff, "Cardiovascular fitness and thermoregulation during prolonged exercise in man" British journal of sports medicine, vol. 23, No. 2 (1989), pp. 109-114.

* cited by examiner

*Primary Examiner* — James H Alstrum-Acevedo
*Assistant Examiner* — Erinne R Dabkowski
(74) *Attorney, Agent, or Firm* — K&L Gates LLP

(57) ABSTRACT

The present invention relates to a method of enhancing endurance of a human subject through administration of alanyl-glutamine or alanyl-glutamine salt. The invention includes unexpected discovery of alanyl-glutamine or alanyl-glutamine salt enhancing durability and endurance of human subject independent of an increase in the blood glutamine level.

8 Claims, 11 Drawing Sheets

Figure 1: a: Plasma Glutamine Concentrations. A significant trial effect was seen between T2 and T5. # = significant difference compared to BL and DHY; a = significant difference compared to T2, T3, and T4. b: AUC Glutamine. * = Significantly different from T2.
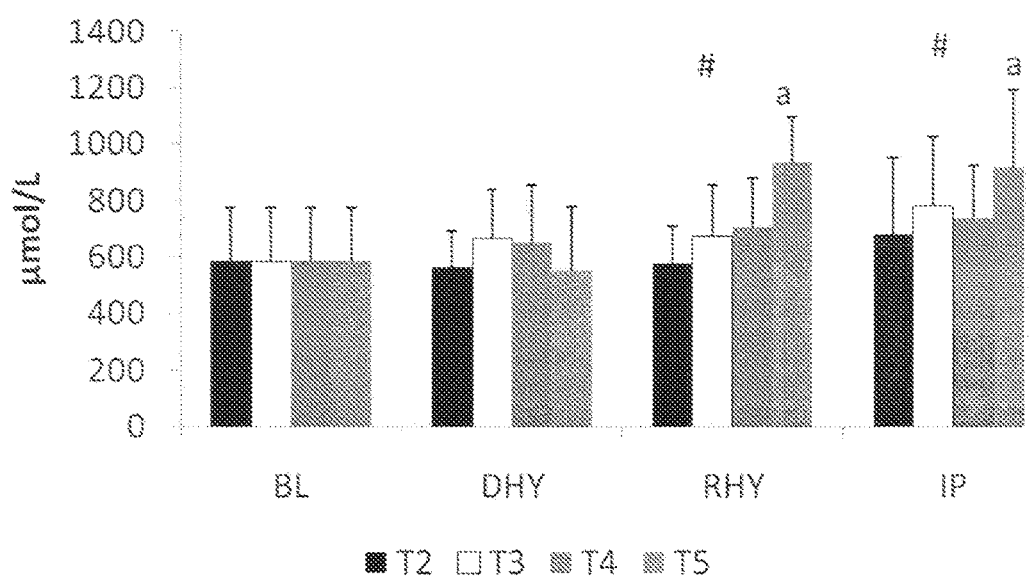
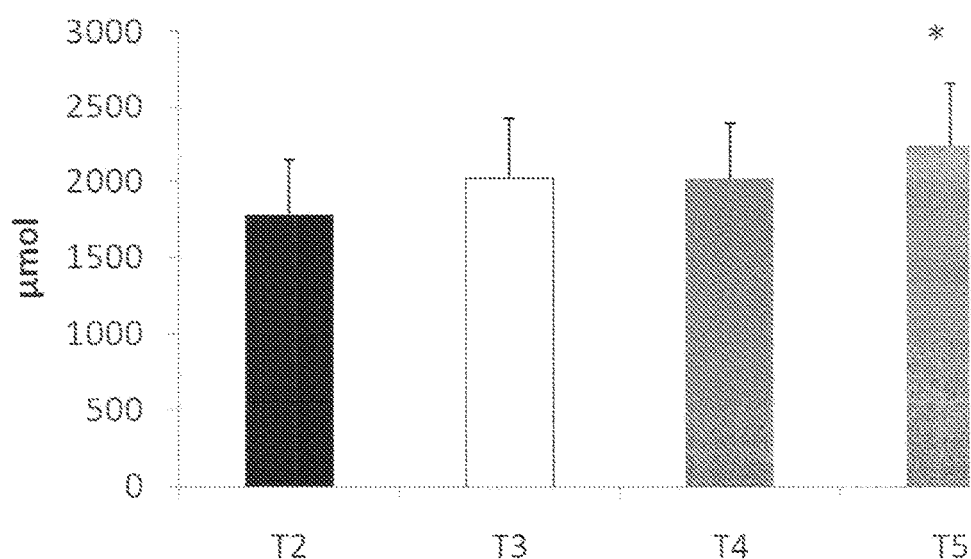

Figure 2: a: Time to Exhaustion.  * Significant compared to all other trials.  b: Δ Time to Exhaustion.  * = Significant compared to ΔT2.
a
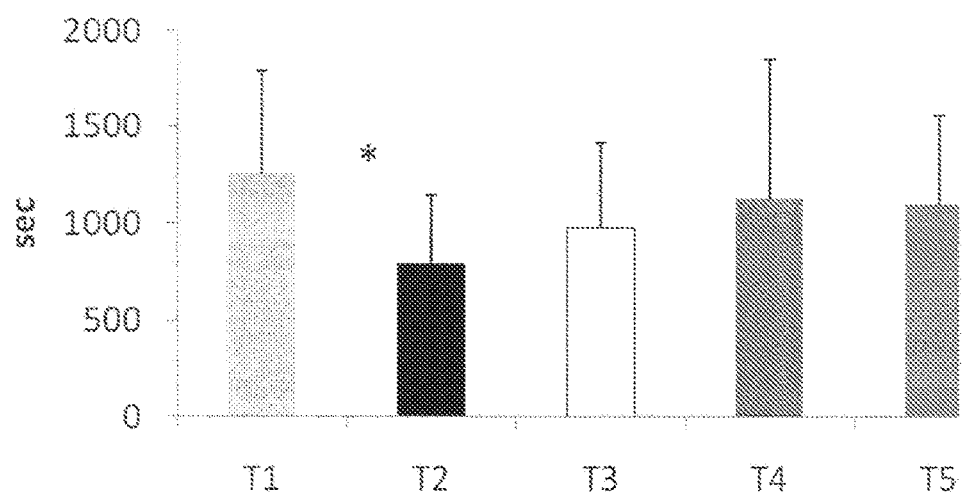
b
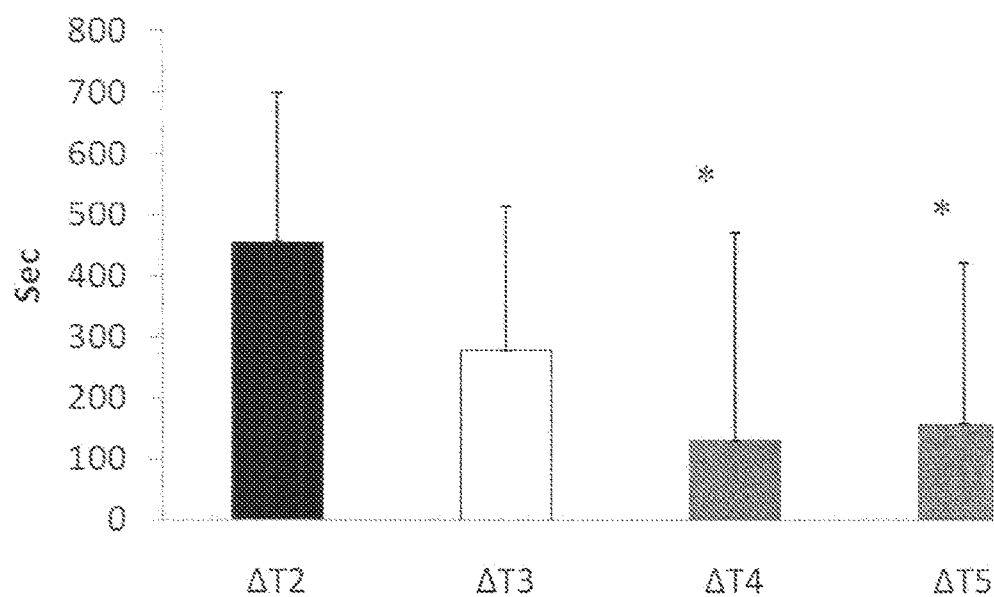

Figure 3: a: Serum Aldosterone Response. # = significant compared to BL and DHY. b: AUC Aldosterone.
a
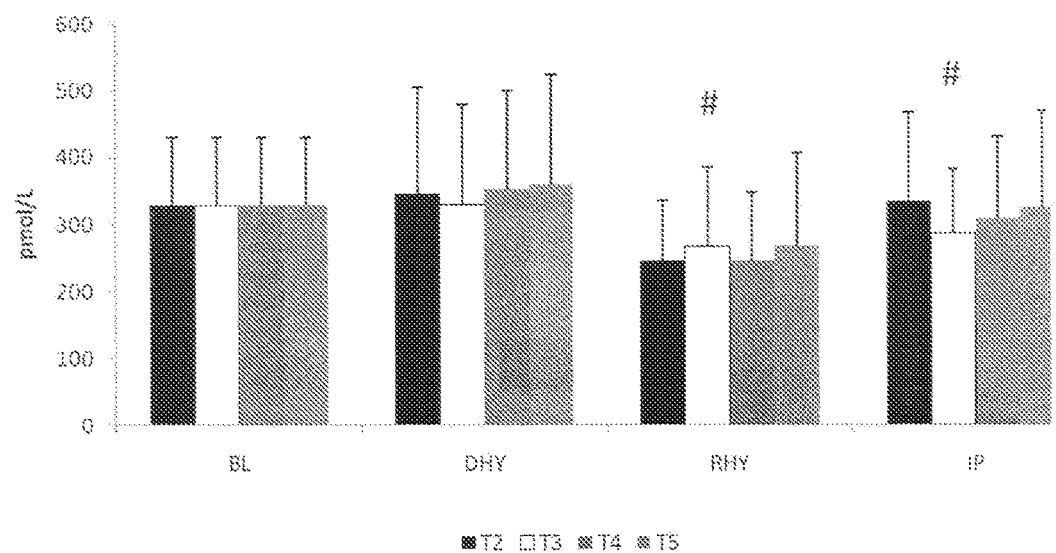
b
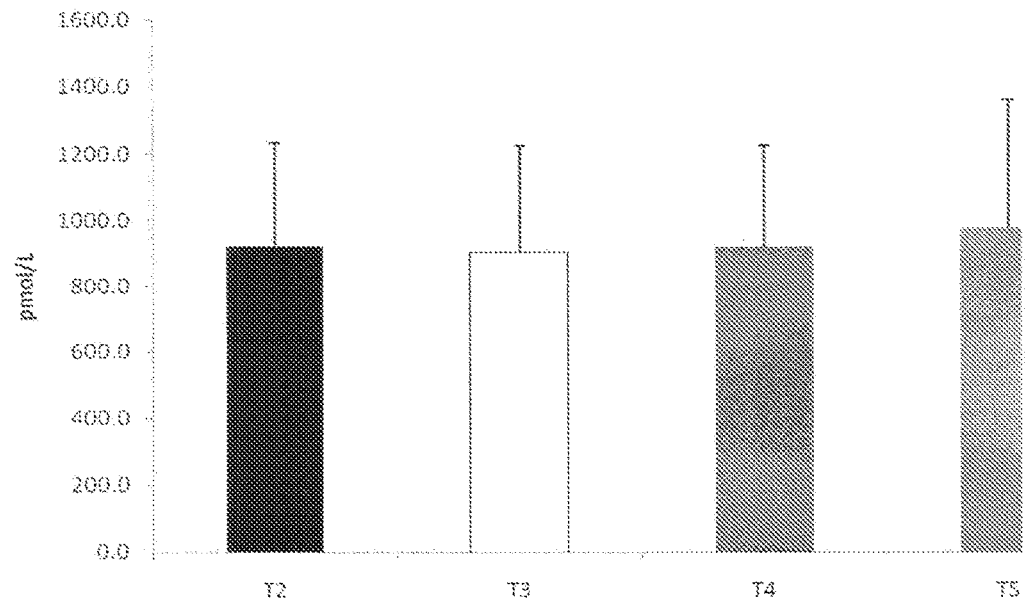

Figure 4: a: C-Reactive Protein Response. * = significant effect at BL. A significant effect was seen between T2 and T4. b: AUC C-Reactive Protein.
a.
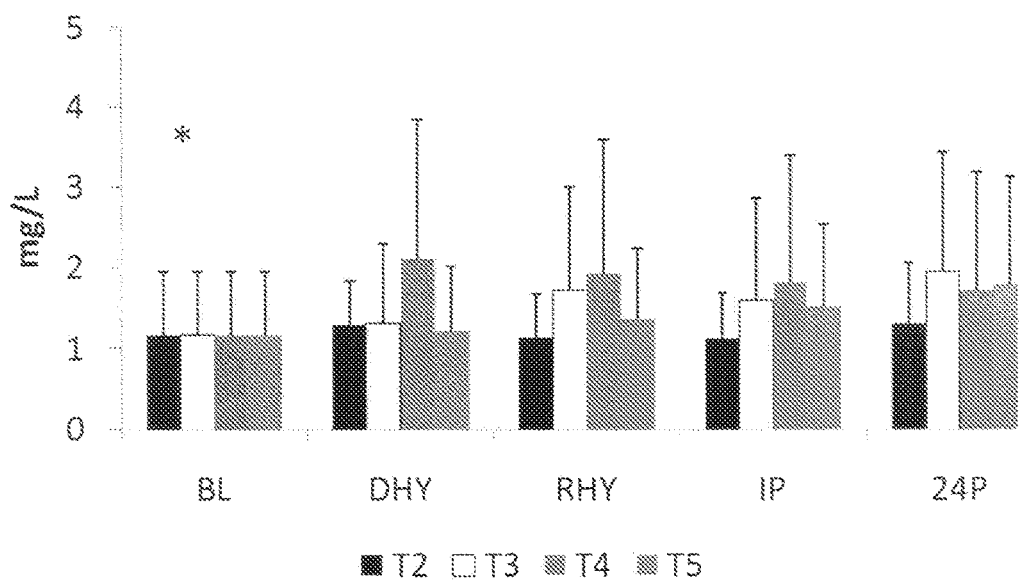
b.
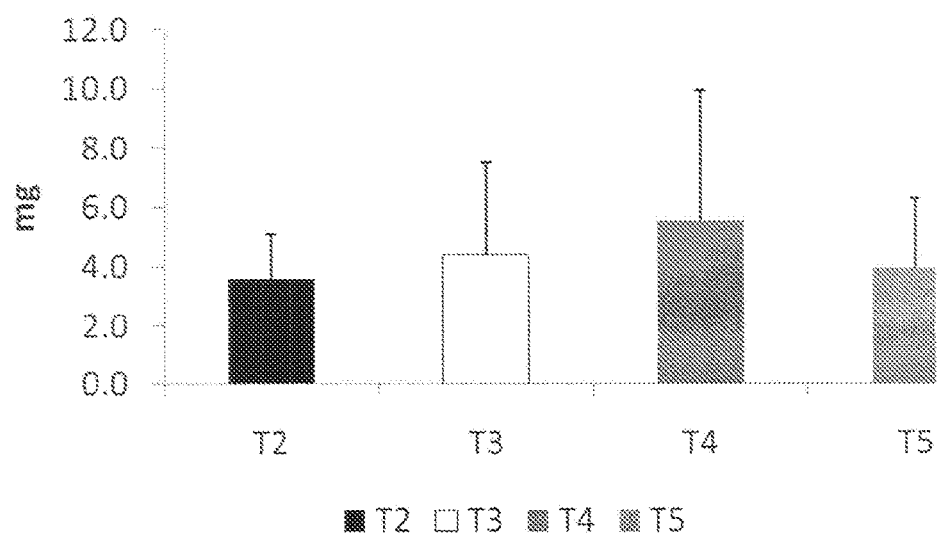

Figure 5: a. IL-6 Response.  # = significant compared to BL, DHY and 24P; * significant compared to BL and 24P. b. AUC-IL-6.
a.
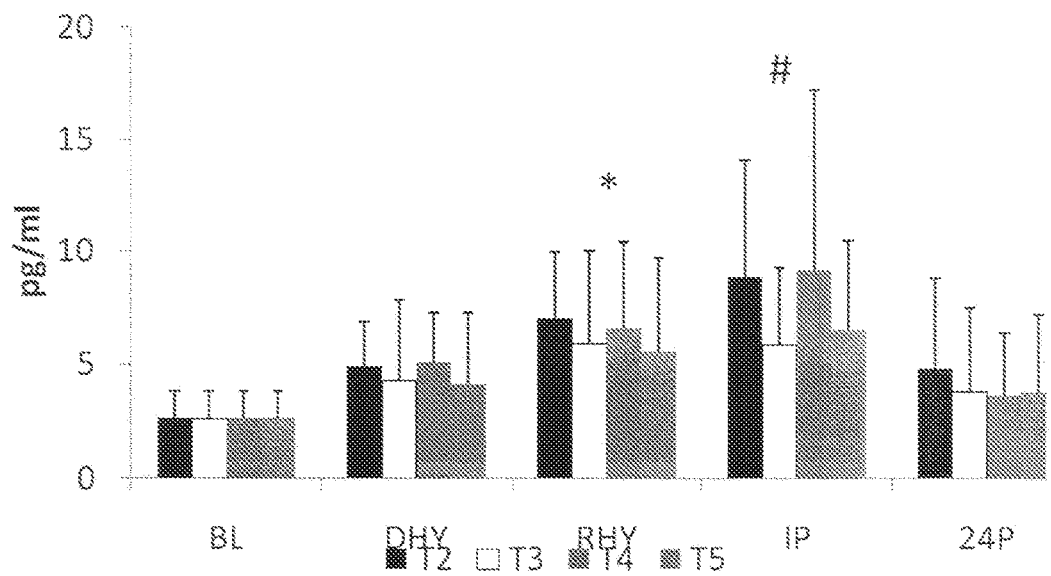
b.
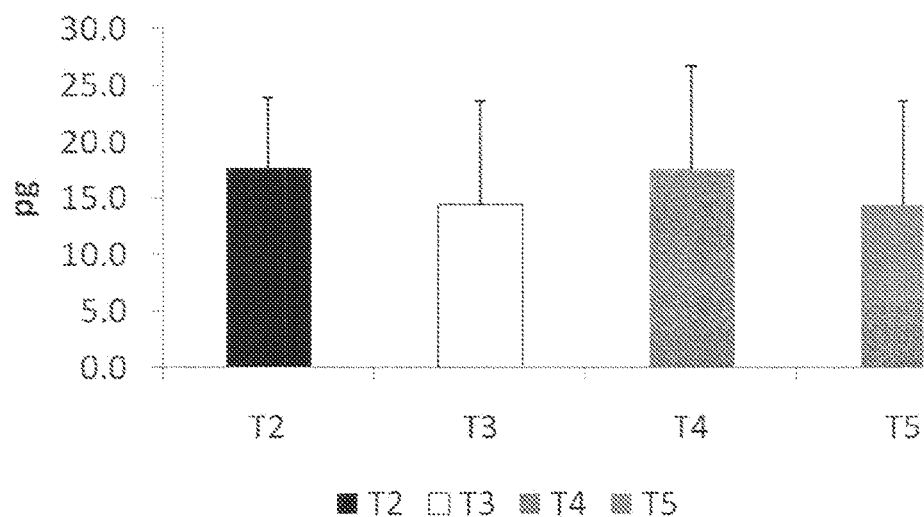

Figure 6: MDA Response. # = significant compared to DHY, RHY, IP, and 24P; A significant effect was seen in T3 and T5 compared to T2 and T4.
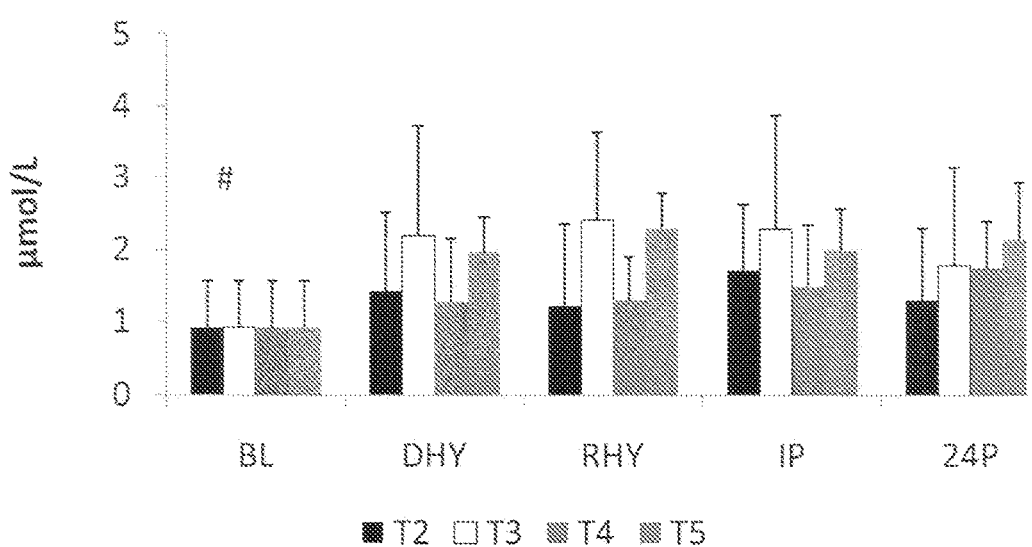

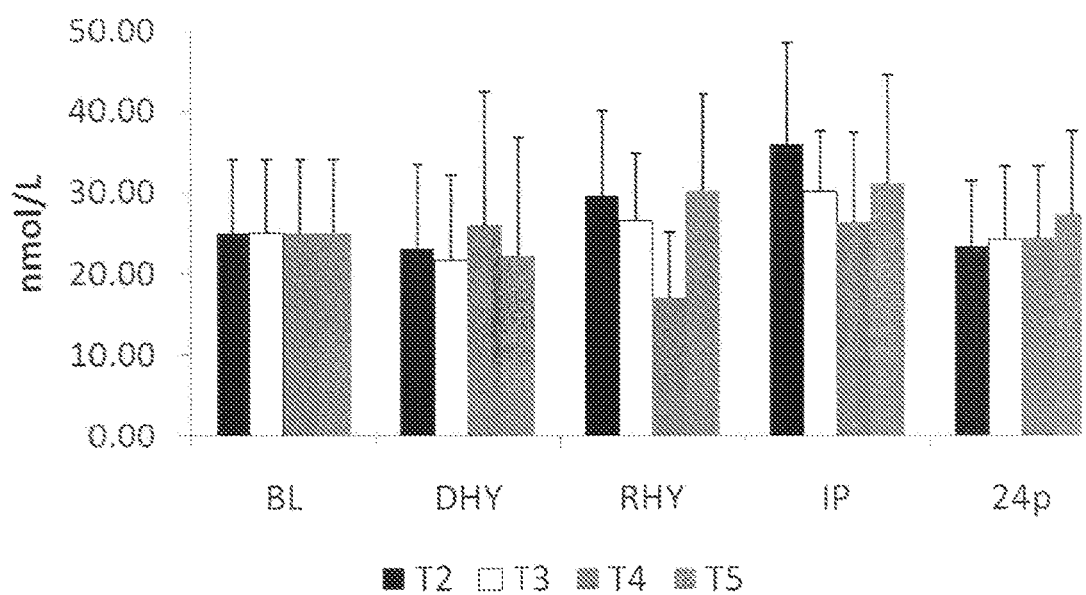
Figure 7: Testosterone Response

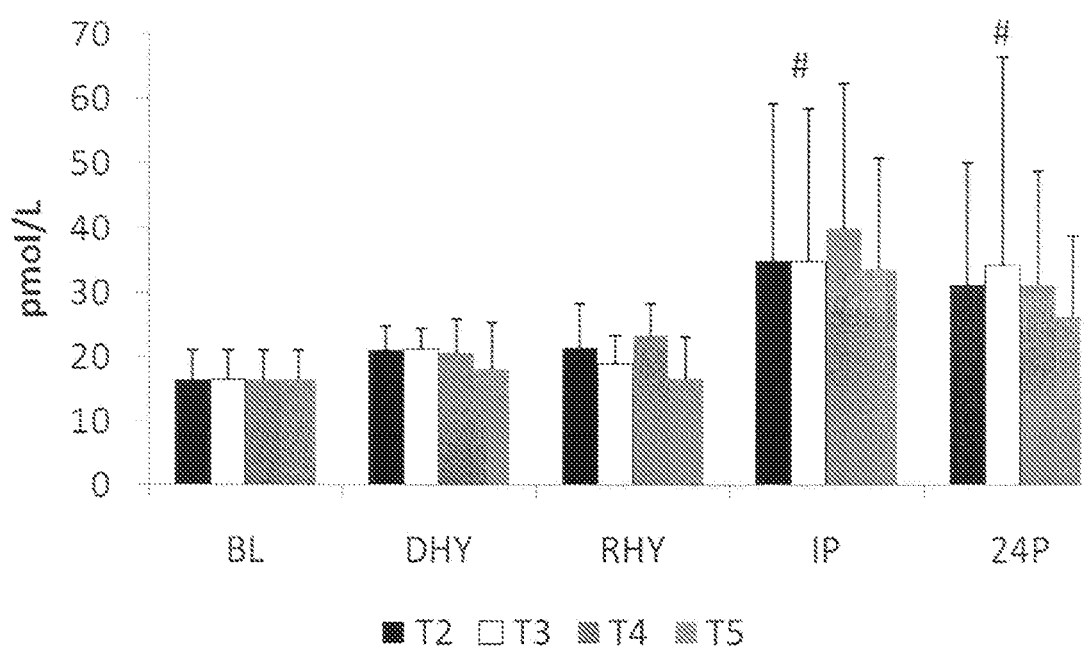
Figure 8: ACTH Response.  # = significant compared to BL, DHY, and RHY

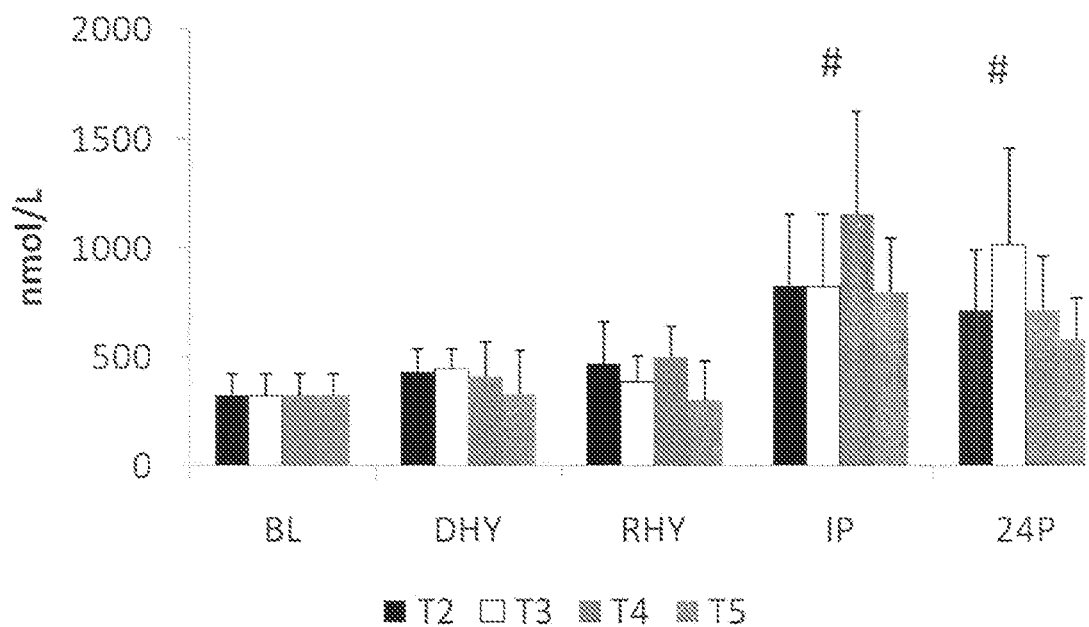
Figure 9: Cortisol Response.   # = significant compared to BL, DHY, and RHY

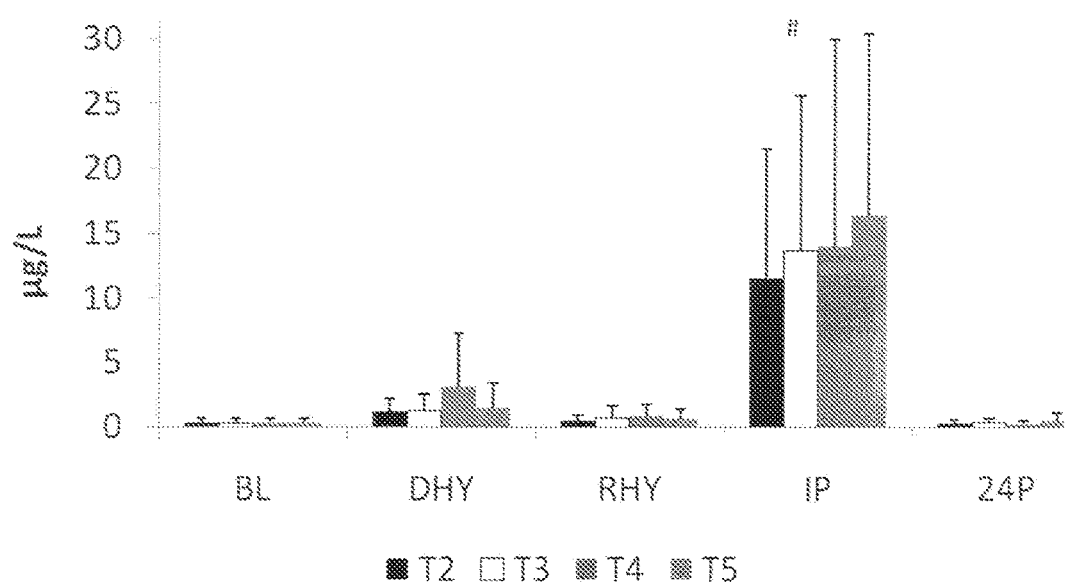
Figure 10: Growth Hormone Response. # = significant compared to BL, DHY RHY, and 24P

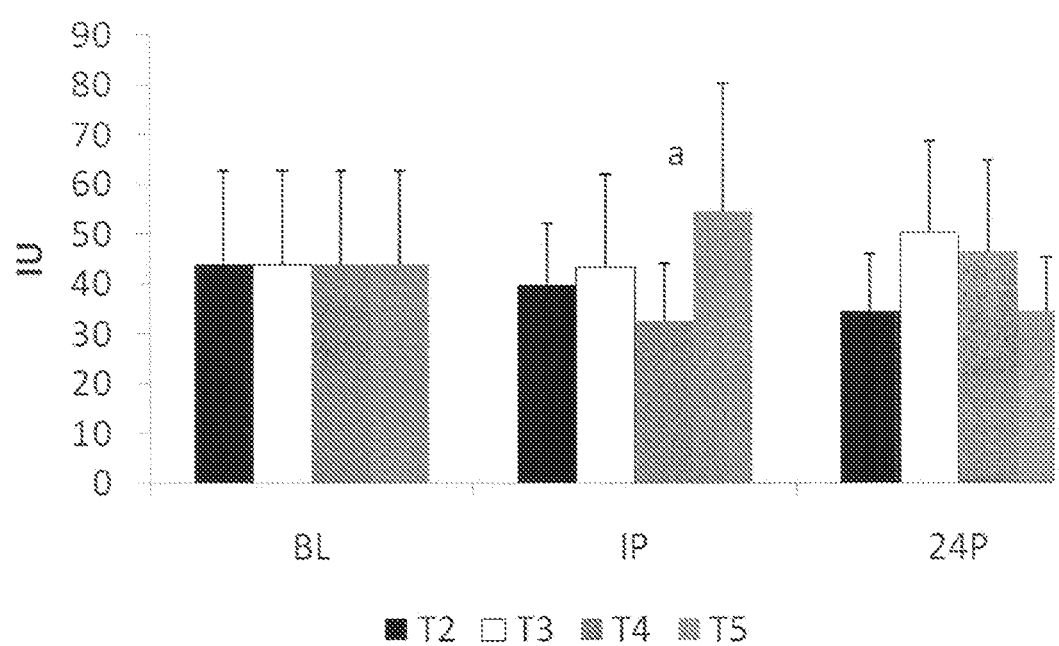
Figure 11: Creatine Kinase Response. a = significant difference between T4 and T5.

METHOD TO ENHANCE ENDURANCE

CROSS-REFERENCE TO RELATED APPLICATION

The application is the U.S. National Phase of International Application No. PCT/US2010/055638, filed Nov. 5, 2010, which claims priority under 35 U.S.C. 119(e) to U.S. Provisional Application No. 61/259,031, filed on Nov. 6, 2009, the contents of which are incorporated by reference herein.

FIELD OF THE INVENTION

The present invention relates to a method to enhance endurance which is characterized by administering alanyl-glutamine or its salt.

BACKGROUND

In recent years, as interest in health grows, the interest in aerobic endurance exercises such as marathon, jogging, cycling, and so on has grown. On the other hand, in the stressful society of modern age, it is also true that, many people are unable to find enough time to exercise due to long working hours and so on, lack of energy to exercise due to exhaustion from day-to-day overwork, or are unsuccessful in continuing to exercise even if they try. Moreover, every year, more school children are losing endurance as more of them become obese, which has become a serious social problem. For this reason, a method to enhance endurance easily, safely and effectively is strongly desired.

Understanding the above background, the development of food ingredients that enhance durability is underway. For instance, proanthocyanidin and lycopene (JP 2003-334022 A), an extract of crataegus cuneata (JP H8-47381 A), and so on, cacaonib (JP 2006-282576 A), catechin (JP 2005-89384 A), olive oil (JP 2009-161459 A) and the like have been reported as ingredients that enhance durability.

Alanylglutamine is a dipeptide comprising two amino acids called alanine and glutamine ("Clinical Science," 1988, Vol. 75, No. 5, p. 438-8; "L-Alanyl-L-Glutamine," Kyowa Hakko Kogyo, 2006, p. 1; WO2007/108530).

BRIEF DESCRIPTION OF THE DRAWINGS

FIG. 1a shows plasma glutamine concentrations of trial groups T2-T5 at measurement points BL, DHY, RHY, and IP.

FIG. 1b shows AUC of glutamine concentration of trial groups T2-T5.

FIG. 2a shows time to exhaustion of trial groups T1-T5.

FIG. 2b shows the difference in time to exhaustion between T1 and each of T2-T5.

FIG. 3a shows serum aldosterone concentrations of trial groups T2-T5 at measurement points BL, DHY, RHY, and IP.

FIG. 3b shows AUC of serum aldosterone concentration of trial groups T2-T5.

FIG. 4a shows C-reactive protein concentrations of trial groups T2-T5 at measurement points BL, DHY, RHY, IP, and 24P.

FIG. 4b shows AUC of C-reactive protein concentration of trial groups T2-T5.

FIG. 5a shows IL-6 concentrations of trial groups T2-T5 at measurement points BL, DHY, RHY, IP, and 24P.

FIG. 5b shows AUC of IL-6 concentration of trial groups T2-T5.

FIG. 6 shows MDA concentrations of trial groups T2-T5 at measurement points BL, DHY, RHY, IP, and 24P.

FIG. 7 shows testosterone concentrations of trial groups T2-T5 at measurement points BL, DHY, RHY, IP, and 24P.

FIG. 8 shows ACTH concentrations of trial groups T2-T5 at measurement points BL, DHY, RHY, IP, and 24P.

FIG. 9 shows cortisol concentrations of trial groups T2-T5 at measurement points BL, DHY, RHY, IP, and 24P.

FIG. 10 shows growth hormone concentrations of trial groups T2-T5 at measurement points BL, DHY, RHY, IP, and 24P.

FIG. 11 shows creatine kinase responses of trial groups T2-T5 at measurement points BL, IP, and 24P.

DETAILED DESCRIPTION

It is also known that, generally, a dipeptide not only physiologically functions as the dipeptide-constituting amino acids alternatively but also provides a variety of effects that an amino acid alone cannot. The present inventors studied functions of alanylgultanine and discovered unexpectedly that alanylglutamine enhances durability independently of an increase in the blood glutamine level, which completed the present invention.

In other words, the present invention is associated with a method of enhancing durability characterized by administrating alanylglutamine or its salt.

In the present invention, alanine and glutamine, which are alanylgultamine-constituting amino acids, may be the L-type or D-type; however, the L-type is preferable.

Salts of alanylgultamine include acid-added salts, metal salt, ammonium salts, organic amine-added salts, amino acid-added salts, and so on.

Acid-added salts include salts formed with inorganic acids such as salts of hydrochloric acid, sulfuric acid, nitric acid, phosphoric acid, and so on, as well as salts formed with organic acids such as acetic acid, maleic acid, fumaric acid, citric acid, malic acid, lactic acid, alpha-ketoglutal acid, gluconic acid, caprylic acid, and so on.

Metal salts include alkali metal salts formed with sodium, potassium, and so on; alkali earth metal salts formed with magnesium, calcium, and so on; and aluminum salts as well as zinc salts, and so on.

Ammonium salts include salts formed with ammonium, tetramethylammonium, and so on.

Organic amine-added salts include salts of morpholine, piperizine, and so on.

Amino acid-added salts include salts formed with glycine, phenylalanine, lysine, asparagic acid, glutamic acid, and so on.

Alanylglutamine may be manufactured by any of the methods comprising synthesis, enzyme method, fermentation, and so on.

Methods for manufacturing alanylglutamine include those described in, for example, Bulletin of the Chemical Society of Japan, 34, 739 (1961, 35, 1966 (1962), 37, 200 (1964), European Patent No. 311057, German Patent No. 3206784, JP 1-16-234715 A, and WO2004/058960.

For alanylglutamine, a commercial product (manufactured by Kyowa Hakko Bio Co., Ltd, Kokusan Kagaku Co., Ltd., or Bachem Corporation) may be used.

In the present invention, alanylglutamine or its salt is administered to a person who needs to enhance his or her durability.

The subject of administration is not limited to sports players; it can be administered to anyone of any age and gender without any particular limitation as long as the person is healthy.

In the present invention, there is no particular limitation to the types of exercise for which durability can be enhanced; however, the types include, for example, aerobic exercises such as walking, jogging, marathon, aerobics, cycling, mountain climbing, swimming, and so on.

In the method of the present invention, alanylglutamine or its salt alone may be administered; however, it is desirable that it be administered in various types of formulations.

The formulation contains alanylglutamine or its salt as its effective component; however, it may also contain other components that are effective for other optional treatments. Moreover, the formulation may be made by any method known in the technical field of pharmacology in which effective components are mixed with one or more pharmacologically allowable carriers.

The desirable administration mode to be used is the most effective form in the treatment, which may be oral administration or non-oral administration such as, for instance, intravenous, peritoneal, or subcutaneous forms. However, oral administration is desirable.

The form of the preparation to be administered may be, for example, an oral preparation such as tablets, powder, granules, pills, suspensions, emulsions, infusions, decoctions, capsules, syrups, liquids, elixirs, extracts, tinctures, fluidextracts, and so on or non-oral preparation such as injection, intravenous injections, creams, and suppositories, and so on. However, an oral preparation is desirable.

In manufacturing of oral preparation, additives such as excipients, binders, disintegrants, amplifiers, dispersants, suspensions, emulsifiers, diluted solutions, buffer solutions, anti-oxidants, bacterial agents, and so on may be used.

A liquid-type drug such as syrup, which is suitable for oral administration, may be formulated by the addition of water; sugar such as cane sugar, sorbitol, fructose, and so on; glycols such as polyethylene glycol, propylene glycol, and so on; oils such as sesame oil, olive oil, soybean oil, and so on; antiseptics such as esters of p-hydroxybenzoate, and so on; preservatives such as derivatives of paraoxybensoate such as methyl paraoxybenzoate and the like and sodium benzoate and so on; and flavors such as strawberry, pepper mint, and so on.

Preparations suitable for oral administration, for example, tablets, powder, and granules, and so on may be formulated by the addition of sugars such as lactose, white sugar, glucose, cane sugar, mannitol, sorbitol, and so on; starch such as potatoes, wheat, corns, and so on; inorganic substances such as calcium carbonate, calcium sulfate, sodium hydrogen carbonate, sodium chloride, and so on; excipients of powdered plant in the form of crystal cellulose, powdered glycyrrhiza, powdered Gentiana Lucia, and so on; disintegrants such as starch, agar, powdered gelatin, crystal cellulose, sodium carboxymethyl cellulose, calcium carboxymethyl cellulose calcium carbonate, sodium hydrogen carbonate, sodium arginate, and so on; lubricants such as magnesium stearate, talc, hydrogenated vegetable oil, Macrogoal, silicone oil, and so on; binders such as polyvinyl alcohol, hydroxypropyl cellulose, methyl cellulose, ethyl cellulose, caboxyethyl cellulose, gelatin, starch glue fluid, and so on; surfactants such as fatty acid esters, and so on; and plastics such as glycerine, and so on.

Moreover, the preparations which are suitable for oral administration, may also be added with general additives that are generally used for foods and beverages, for example, sweeteners, coloring agents, preservatives, thickening agents, antioxidants, color forming agents, bleach, antifungal agents, gum base, bittering agents, enzymes, glazing agents, acidifier, condiments, emulsifier, reinforcement, agents for manufacturing purposes, flavoring agents, spice extracts, and so on.

Preparations that are suited to oral administration may be used as they are, or in the form of, for example, powdered foods, sheet foods, binned foods, canned foods, retort packaged foods, capsules, tablets, fluids and health drinks as durability enhancing health foods, foods with health claims, nutritional supplements, or foods for specified health uses to enhance durability.

Preparations suited to non-oral administration, for example, sterile aqueous solutions, comprise alanylglutamine or its salt which is preferably isotonic with the recipient's blood. For example, injection solutions are prepared by the use of a carrier and the like comprising a salt solution, glucose solution, or a mixture of a salt solution and a glucose solution.

Moreover, these non-oral administration preparations may also contain any one or more supplemental components selected from diluents, preservatives, excipients, disintegrants, amplifiers, binders, surfactants, plastics, and the like.

The concentration of alanylglutamine or its salt contained in the preparation used in the method of the present invention may be optionally selected in accordance with the type of preparation and the expected efficacy from the administration of said preparation and the like. Nonetheless, in the case of orally administered preparation is, for example, the concentration of alanylglutamine or its salt is normally 0.1-100% by weight, preferably 0.5-70% by weight, and most preferably 1-50% by weight.

The dosage frequency of alanylglutamine or its salt varies depending on the age, weight, and expected efficacy of the subject. Nevertheless, an adult is dosed with alanylglutamine or its salt once to several times per day so that, normally, the dosage stays at 5 mg-30000 mg, preferably 50 mg-5000 mg, and more preferably 500 mg-3000 mg.

There is no particular limit to the timing of dosage. However, it is preferable that it be dosed prior to or during endurance exercise, more preferably, prior to durability exercise.

There is also no particular limit to the duration of dosage. Nonetheless, the normal duration is one day to one year, more preferably two weeks to three months.

Experimental examples showing the efficacy of alanylglutamine on durability enhancement are described below.

EXAMPLES

Examination of the Efficacy of Acute L-Alanyl-L-Glutamine Ingestion During Hydration Stress during Endurance Exercises Methods:

Subjects:

Ten men (20.8±0.6 yrs; 176.8±7.2 cm; 77.4±10.5 kg; 12.3±4.6% body fat) volunteered to participate in this study. Following explanation of all procedures, risks and benefits, each subject provided informed consent prior to participation in this study. The Institutional Review Board of the College approved the research protocol. Subjects were not permitted to use any additional nutritional supplements for at least four weeks prior to the study. Screening for supplement use was accomplished via a health history questionnaire completed during the subject recruitment phase.

Protocol

Subjects reported to the Human Performance Laboratory (HPL) on six separate occasions. During the initial session, subjects performed a graded maximal aerobic capacity test ($VO_2$ max) on an electromagnetically braked cycle ergometer (Ergo 800, SensorMedics, Inc., Yorba Linda, Calif.). The $VO_2$ max test was administered to establish workloads for subsequent endurance tests. $VO_2$, RER, and $V_E$ were measured using the MedGraphics ULTIMA metabolic system (MedGraphics Corporation, St. Paul, Minn.). Gas analyzers were calibrated using gas provided by MedGraphics Corporation: 1) calibration gas: 5% $CO_2$, 12% $O_2$, balance $N_2$; and 2) reference gas: 21% $O_2$, balance $N_2$. Gas calibration was conducted before each trial. Heart rate (HR) was measured using a wireless HR monitor (Pacer, Polar CIC, Inc., Port Washington, N.Y.).

On four of the five subsequent visits to the HPL, subjects dehydrated to 2.5% of their baseline body mass. On the occasion that a dehydration protocol was not employed, subjects reported to the HPL in a euhydrated state to provide a baseline blood draw and perform the exercise protocol. This trial (T1) provided baseline performance data for how subjects performed in optimal conditions without hydration stress. All performance comparisons were made to this trial. In one trial (T2) subjects achieved their goal weight (−2.5% of baseline body weight) and rested in a recumbent position for 45 minutes before commencing the exercise session. In the subsequent three trials subjects reached their goal weight (−2.5% of baseline body mass) and then rehydrated to −1.5% of their baseline body mass by drinking either water (T3) or two different doses (T4 and T5) of the alanyl-glutamine (ALA-GLU) supplement (0.05 g·kg$^{-1}$ and 0.2 g·kg$^{-1}$, respectively). During the hydration trials (T3-T5), the exercise protocol began 45 minutes following reaching their goal weight. During this time frame, subjects were rehydrated. The order of the trials was randomly determined.

Dehydration Protocol

Prior to the onset of the study, subjects reported to the HPL for determination of baseline body mass. These measures were performed on nonconsecutive days and occurred approximately one week before the start of experimental testing. Subjects were weighed during these visits in a postabsorptive, euhydrated state to establish a baseline body weight. A urine sample was analyzed for osmolality ($U_{osm}$) by freezing point depression and urine specific gravity ($U_{sg}$) by refractometry to document euhydration on all preliminary days. Euhydration was defined as $U_{sg} \leq 1.020$ (Armstrong et al., 1994).

On the night before testing (5 p.m.), subjects reported to the HPL for weighing and urine specific gravity measures to ascertain that subjects were euhydrated. Subjects were then instructed to not consume any food or water until the next day when they reported back to the HPL (7 a.m.). This resulted in an average body mass change of −1.03±1.3%. On the morning of trials T2-T5, subjects reporting to the HPL were weighed and began the active dehydration protocol to achieve the desired weight loss. The active dehydration protocol required subjects to walk on a motorized treadmill at 3.4 mi·h$^{-1}$ and at a 2% incline. Subjects were fully clothed in a training suit (long cotton heavy weight fleece sweat pants and top). Nude body weight, heart rate, and rating of perceived exertion were monitored at 20-minute increments. The subjects continued to walk until they (a) had lost 2.5% of their body mass, (b) met preset safety criteria, (c) displayed signs or symptoms of an exercise-induced heat illness, or (d) requested to stop due to exercise fatigue. At the end of the dehydration period, a urine specimen and blood samples were obtained. Dehydration was verified by measuring urine specific gravity and both urine and plasma osmolality. The time necessary to reach the goal body mass (−2.5% weight loss) was 62.5±44.2 min. There were no significant differences in time to reach goal body mass between trials.

Supplement Schedule

Subjects consumed the supplement or placebo (water) following the dehydration protocol as part of their rehydration to −1.5% of their baseline body mass. The L-alanyl-L-glutamine supplement (0.2 g·kg$^{-1}$ or 0.05 g·kg$^{-1}$) (Kyowa Hakko USA, New York, N.Y.) was mixed with water and was indistinguishable in appearance and taste from the placebo.

Time to Exhaustion Test

After dehydration and rehydration (except during trial T2), subjects began the exercise protocol. Subjects exercised at a workload that elicited 75% of their $VO_2$ max on a cycle ergometer. Subjects were encouraged to give their best effort during each trial, and were verbally encouraged throughout each exercise trial. Oxygen consumption, minute ventilation, respiratory exchange ratio, and heart rate were measured continuously. Heart rate and blood pressure were recorded before and at the conclusion of exercise. Time to exhaustion was determined as the time that the subject could no longer maintain the workload and/or reach volitional exhaustion.

Blood Measures

A baseline (BL) blood draw occurred during T1. No other blood was drawn during that trial. The BL blood sample was drawn following a 15-min equilibration period prior to exercise. During trials T2-T5, blood draws occurred once goal body mass was achieved (DHY), immediately prior to the exercise stress (RHY), and immediately following the exercise protocol (IP). Subjects returned to the laboratory 24 hours post exercise for an additional blood draw (24P). All trial blood samples (DHY, RHY and IP) were obtained using a 20-gauge Teflon cannula placed in a superficial forearm vein using a 3-way stopcock with a male luer lock adapter. The cannula was maintained in the patient using an isotonic saline solution (with 10% heparin). IP blood samples were taken within 15 seconds of exercise cessation. All BL and 24P blood samples were drawn with a plastic syringe while the subject was in a seated position. These blood samples were obtained from an antecubital arm vein using a 20-gauge disposable needle equipped with a Vacutainer® tube holder (Becton Dickinson, Franklin Lakes, N.J.) with the subject in a seated position. Each subjects' blood samples were obtained at the same time of day during each session. Blood samples were collected into two Vacutainer® tubes, one containing SST® Gel and Clot Activator and the second containing EDTA. A small aliquot of whole blood was removed from the second tube and used for microcapillary determination of hematocrit. The remaining blood in that tube was used for hemoglobin and several of the hormonal and biochemical analyses. Hemoglobin measures were performed without freezing, but the remaining plasma was placed into separate 1.8-ml microcentrifuge tubes and frozen at −80° C. for later analysis. The blood in the first tube was allowed to clot at room temperature and subsequently centrifuged at 1500×g for 15 minutes. The resulting serum was placed into separate 1.8-ml microcentrifuge tubes and frozen at −80° C. for later analysis.

Biochemical and Hormonal Analyses

Serum testosterone, cortisol and growth hormone concentrations were determined using enzyme immunoassays (EIA) and enzyme-linked immunosorbent assays (ELISA)

(Diagnostic Systems Laboratory, Webster, Tex.). Serum aldosterone and IL-6 concentrations were determined using an EIA assay (ALPCO Diagnostics, Salem, N.H.). Plasma arginine vasopressin (AVP) concentrations were determined using an EIA assay (Cayman Chemical Co, Ann Arbor, Mich.). Plasma adrenocorticotrophic hormone (ACTH) concentrations were determined using an ELISA assay (ALPCO Diagnostics, Salem, N.H.). Plasma C-reactive protein concentrations were determined using an ELISA assay (Diagnostic Systems Laboratory, Webster, Tex.), and plasma malondialdehyde (MDA) concentrations were determined using an ELISA assay (Cell Biolabs Inc., San Diego, Calif.). Determination of serum immunoreactivity values was made using a SpectraMax340 Spectrophotometer (Molecular Devices, Sunnyvale, Calif.). To eliminate inter-assay variance, all samples for a particular assay were thawed once and analyzed in the same assay run. All samples were run in duplicate with a mean intra-assay variance of <10%. Serum creatine kinase concentrations were analyzed with the use of a spectrophotometer and a commercially available enzymatic kit (Pointe Scientific, Inc, Canton, Mich.).

Hemoglobin was analyzed in triplicate from whole blood using the cyanmethemoglobin method (Sigma Diagnostics, St. Louis, Mo.). Hematocrit was analyzed in triplicate from whole blood via microcentrifugation (IEC micro-MB centrifuge, Needham, Mass.) and microcapillary technique. Plasma volume shifts following the workout were calculated using the formula of Dill & Costill (1974). Plasma glutamine, glucose and lactate concentrations were determined in duplicate with an automated analyzer (Analox GM7 enzymatic metabolite analyzer, Analox Instruments USA, Lunenburg, Mass.). Plasma sodium and potassium concentrations were assessed via ion-selective electrodes (Model984-S; AVL Scientific Corporation, Roswell, Ga.). Plasma and urine osmolality were determined without freezing via freezing point depression osmometer (Model 3320; Micro-Sample Osmometer, Advanced Instruments, Inc., Norwood, Mass.).

Statistical Analysis

Statistical evaluation of performance, hormonal and biochemical changes was accomplished using a repeated measures analysis of variance (ANOVA). In the event of a significant F-ratio, LSD post-hoc tests were used for pairwise comparisons. Prior to the ANOVA, all data were assessed and met assumptions for normal distribution, homogeneity of variance, and sample independence. Plasma volume shifts and Δ performance comparisons were analyzed using a One-Way ANOVA. One-way ANOVAs were also used to analyze the area under curve (AUC), which was calculated by using a standard trapezoidal technique. Significance was accepted at an alpha level of $p \leq 0.05$. All data are reported as mean±SD.

Results

Urine specific gravity (1.026±0.004), urine osmolality (813±299 mOsm), and plasma osmolality (296.9±4.6 mOsm) at DHY were similar for all trials. These results reflected the overnight fasting and exercise-induced dehydration performed prior to each trial. Plasma glutamine concentrations were significantly higher for all groups at RHY and IP compared to BL and DHY (see FIG. 1a). Glutamine concentrations for T5 were significantly higher at RHY and IP than T2-T4. AUC analysis showed a significantly higher glutamine concentration for T5 at all time points compared to the other experimental trials (see FIG. 1b).

Time to exhaustion was significantly lower during T2 than any other experimental trial (see FIG. 2a). When examining Δ performance changes (difference between each experimental trial and T1), significantly greater times to exhaustion were seen during T4 and T5 compared to T2 (see FIG. 2b). No other differences were noted between trial comparisons. Cardiovascular changes during exercise are depicted in Table 1. No significant differences in either resting or immediate post-exercise heart rates were seen between trials. No significant differences in resting blood pressure were seen between trials, however blood pressures at IP were significantly lower at T2 and T3 compared to T1. No other differences were seen in the blood pressure response between trials. No changes in RER were seen between trials.

Significant effects were seen in both plasma lactate and glucose responses to the exercise protocol (Table 2). Significant increases were seen at IP in both of these variables compared to all other time points. However, no significant differences were seen between trials. A main effect for time was also seen in plasma osmolality. Plasma osmolality at IP was significantly elevated compared to BL and RHY only. No other significant differences were noted. In addition, no differences between trials were observed in plasma osmolality. Plasma potassium was significantly elevated at IP compared to BL, DHY and RHY. No other differences were noted and no differences between trials were observed. Plasma sodium concentrations at IP and DHY were significantly greater than that observed at BL and RHY. Plasma sodium concentrations were significantly greater at T2 compared to all other experimental conditions. Plasma sodium concentrations were also significantly greater for T2 than all other experimental trials at RHY and IP. AUC analysis also demonstrated a significantly greater sodium concentration for T2 compared to all other trials.

The scrum aldosterone response to the experimental trials can be seen in FIG. 3. Aldosterone concentrations at RHY and IP were significantly lower than that seen at BL and DHY (FIG. 3a). No other significant differences were noted and no significant interactions were observed. AUC analysis also revealed no significant differences between trials.

No significant differences were observed between trials in changes to C-reactive protein, IL-6, and MDA concentrations (see FIGS. 4-6). Significant time effects were observed for both C-reactive protein and MDA. BL concentrations for both of these variables were significantly lower than all other time points. A significant trial effect was also observed for C-reactive protein. Concentrations of C-reactive protein were significantly greater for T4 than T2. No other differences were noted. A significant trial effect was seen for MDA between T3 and T5 versus T2 and T4. Comparing changes in IL-6 concentrations revealed a significant time effect. IL-6 concentrations were significantly greater at IP than at BL, DHY, RHY and 24P. In addition, IL-6 concentrations at RHY were significantly different than that seen at BL and 24P. AUC analysis for C-reactive protein, IL-6 and MDA did not reveal any significant differences between trials.

No significant differences from BL were seen in the testosterone response to exercise and dehydration stress during any experimental trial (FIG. 7). A significant time effect was seen in both the ACTH and cortisol response to the exercise and dehydration protocol (FIGS. 8 and 9, respectively). When collapsed across trials, significant elevations in cortisol, concentrations were seen at IP and 24P compared to BL, DHY and RHY. No other significant differences were noted and no trial effect was observed. In addition, no significant interactions were observed for any of these hormones. A significant main effect for time was also seen for growth hormone. When assessed across trials, growth hormone concentrations were significantly elevated at IP compared to all other time points (FIG. 10). No other differences were observed. AUC analyses for testosterone, ACTH, cortisol and growth hormone did not result in any significant differences between trials. Creatine kinase concentrations are shown in FIG. 11. A significant difference was seen between T4 and T5 at IP. No other significant differences were observed.

Plasma volumes decreased −5.45±11.38% at DHY for all experimental trials, plasma volumes were decreased at RHY (−6.78±11.27%) for all experimental trials and continued to decrease at IP (−21.44±10.54%). However the difference between trials was not significant. Blood variables were not corrected for plasma volume shifts due to the importance of molar exposure at the tissue receptor level.

In FIG. 2a, a significant decrease in exercise endurance duration was seen in T2, in which rehydration was not performed, compared to T1, in which dehydration was not performed. However, there was a trend of inhibiting the decrease in duration of exercise endurance in T3, in which only rehydration was performed, compared to T2. Compared to T3, this trend was even more pronounced in T4 and T5, in which alanyl-glutamine was ingested.

On the other hand, in FIG. 1a, no differences were seen in T2-T5 immediately after dehydration (DHY: before rehydration). However, plasma glutamine concentration significantly increased only in T5, in which a drink containing 0.2 g/kg alanyl-glutamine was ingested, compared to T2-T4. No differences were observed between T3, in which only rehydration was performed, and T4, in which a drink containing 0.05 g/kg alanyl-glutamine was ingested.

These results indicate that alanyl-glutamine has an endurance enhancing effect independent of increases in plasma glutamine concentration.

TABLE 1

Cardiovascular Changes during Exercise Protocol

| Variable | T1 | T2 | T3 | T4 | T5 |
|---|---|---|---|---|---|
| Resting Heart Rate (beats · min$^{-1}$) | 75.7 ± 14.6 | 78.6 ± 15.4 | 72.9 ± 13.8 | 76.7 ± 17.6 | 76.9 ± 15.8 |
| IP Heart Rate (beats·min$^{-1}$) | 180.2 ± 13.8 | 187.8 ± 9.6 | 179.7 ± 18.0 | 183.0 ± 12.5 | 184.2 ± 13.0 |
| Resting SBP (mmHg) | 117.0 ± 6.0 | 112.4 ± 4.8 | 111.5 ± 5.5 | 114.8 ± 5.2 | 113.0 ± 7.7 |
| IP SBP (mmHg) | 167.3 ± 6.0 | 131.3 ± 8.1* | 136.4 ± 20.3* | 150.3 ± 23.0 | 152.5 ± 19.6 |
| Resting DBP (mmHg) | 77.3 ± 3.6 | 74.7 ± 4.8 | 75.4 ± 3.8 | 79.0 ± 2.7 | 77.2 ± 5.9 |
| IP DBP (mmHg) | 88.4 ± 7.0 | 86.0 ± 3.5 | 84.0 ± 9.4 | 88.3 ± 11.6 | 84.8 ± 11.9 |
| RER | 1.12 ± 0.09 | 1.10 ± 0.07 | 1.12 ± 0.07 | 1.08 ± 0.10 | 1.07 ± 0.08 |

IP = immediate post;

SBP = systolic blood pressure;

DBP = diastolic blood pressure.

*= significant difference compared to T1.

All data are reported as mean ± SD.

TABLE 2

Plasma Lactate, Glucose, Osmolality and Electrolyte Response to Exercise

| Variable | Time Point | T2 | T3 | T4 | T5 |
|---|---|---|---|---|---|
| Lactate (mmol · L$^{-1}$) | DHY | 1.9 ± 0.6 | 1.9 ± 0.6 | 2.0 ± 0.6 | 1.7 ± 0.6 |
|  | RHY | 1.8 ± 0.5 | 2.1 ± 0.4 | 2.0 ± 0.5 | 2.1 ± 0.4 |
|  | IP* | 11.1 ± 2.3 | 11.9 ± 2.2 | 9.9 ± 4.2 | 11.7 ± 2.2 |
| Glucose (mmol · L$^{-1}$) | BL | 5.8 ± 1.2 | 5.8 ± 1.2 | 5.8 ± 1.2 | 5.8 ± 1.2 |
|  | DHY | 6.5 ± 1.8 | 6.4 ± 1.1 | 6.4 ± 1.4 | 5.7 ± 1.2 |
|  | RHY | 5.9 ± 1.7 | 6.2 ± 1.1 | 6.4 ± 0.9 | 5.6 ± 1.2 |
|  | IP* | 6.9 ± 1.6 | 8.6 ± 1.5 | 8.4 ± 1.9 | 7.4 ± 2.6 |
| Osmolality (mOsm) | BL | 295 ± 4 | 295 ± 4 | 295 ± 4 | 295 ± 4 |
|  | DHY | 298 ± 5 | 298 ± 5 | 296 ± 4 | 298 ± 6 |
|  | RHY | 298 ± 6 | 293 ± 5 | 292 ± 4 | 294 ± 4 |
|  | IP# | 308 ± 5 | 299 ± 4 | 302 ± 5 | 303 ± 7 |
| Potassium (mmol · L$^{-1}$) | BL | 4.1 ± 0.4 | 4.1 ± 0.4 | 4.1 ± 0.4 | 4.1 ± 0.4 |
|  | DHY | 4.2 ± 0.9 | 4.0 ± 0.3 | 4.1 ± 0.3 | 4.0 ± 0.3 |
|  | RHY | 4.1 ± 0.2 | 4.3 ± 0.3 | 4.3 ± 0.6 | 4.1 ± 0.4 |
|  | IP* | 4.5 ± 0.7 | 4.5 ± 0.5 | 4.4 ± 0.4 | 4.5 ± 0.6 |

TABLE 2-continued

Plasma Lactate, Glucose, Osmolality and Electrolyte Response to Exercise

| Variable | | Time Point | T2 | T3 | T4 | T5 |
|---|---|---|---|---|---|---|
| Sodium ($mmol \cdot L^{-1}$) | BL | | 139.4 ± 1.1 | 139.4 ± 1.1 | 139.4 ± 1.1 | 139.4 ± 1.1 |
| | DHY* | | 141.7 ± 1.1 | 141.3 ± 1.6 | 141.1 ± 2.5 | 141.2 ± 1.4 |
| | RHY | | 141.5 ± 1.5@ | 139.6 ± 1.9 | 138.7 ± 1.9 | 138.7 ± 1.6 |
| | IP# | | 144.0 ± 2.2@ | 140.6 ± 1.8 | 140.7 ± 2.0 | 140.2 ± 1.3 |

*= Significant compared to all other time points.
# = Significant compared to BL and RHY.
@ = significantly compared to T3-T5.
BL = baseline;
DHY = dehydration;
RHY = rehydration;
IP = immediate post-exercise.

What is claimed is:

1. A method of enhancing endurance during exercise of a dehydrated human subject, comprising the step of:
   administering an effective amount of alanyl-glutamine or a salt thereof to the dehydrated human subject in a single dose,
   wherein the dehydrated human subject is at least dehydrated at the beginning of the exercise by a loss of more than 1.5% of the dehydrated human subject's baseline body mass, and
   the exercise elicits the dehydrated human subject a workload of at least 75% of the dehydrated human subject's $VO_2$, max.

2. The method of claim 1, wherein the exercise is aerobic exercise.

3. The method of claim 1, wherein alanyl-glutamine or a salt thereof is L-alanyl-L-glutamine or a salt thereof.

4. The method of claim 1, wherein the human subject is an adult human subject.

5. The method of claim 1, wherein the effective amount of alanyl-glutamine or a salt thereof administered to the adult human subject is in an amount of at least 5 mg and at most 30,000 mg at a time.

6. The method of claim 1, wherein the effective amount of alanyl-glutamine or a salt thereof administered to the adult human subject is in an amount of at least 50 mg and at most 5,000 mg at a time.

7. The method of claim 1, wherein the effective amount of alanyl-glutamine or a salt thereof administered to the adult human subject is in an amount of at least 500 mg and at most 3,000 mg at a time.

8. A method for increasing the time to exhaustion during exercise of a dehydrated human subject, comprising the step of:
   administering an effective amount of alanylglutamine or a salt thereof to the dehydrated human subject in a single dose,
   wherein the dehydrated human subject is at least dehydrated at the beginning of the exercise by a loss of more than 1.5% of the dehydrated human subject's baseline body mass, and the exercise elicits the dehydrated human subject a workload of at least 75% of the human subject's $VO_2$ max.

* * * * *